(12) United States Patent
Wardlaw

(10) Patent No.: US 6,866,823 B2
(45) Date of Patent: Mar. 15, 2005

(54) APPARATUS FOR ANALYZING BIOLOGIC FLUIDS

(75) Inventor: Stephen C. Wardlaw, Old Saybrook, CT (US)

(73) Assignees: Robert A. Levine, Guilford, CT (US); Wardlaw Partners LP, Lyme, CT (US)

( * ) Notice: Subject to any disclaimer, the term of this patent is extended or adjusted under 35 U.S.C. 154(b) by 380 days.

(21) Appl. No.: 09/981,581

(22) Filed: Oct. 17, 2001

(65) Prior Publication Data

US 2002/0028158 A1 Mar. 7, 2002

Related U.S. Application Data

(62) Division of application No. 09/255,673, filed on Feb. 23, 1999.
(60) Provisional application No. 60/077,210, filed on Mar. 7, 1998.

(51) Int. Cl.[7] .................. G01N 33/48; G01N 33/00; G01N 21/76; G01N 21/29; G01N 15/06
(52) U.S. Cl. .................. 422/82.05; 422/50; 422/52; 422/55; 422/58; 422/68.1; 422/73; 422/82.06; 422/82.07; 422/82.08; 422/82.09; 422/82.11; 422/100; 422/102; 422/104; 436/63; 436/66; 436/69; 436/70; 436/164; 436/165; 436/169; 436/172; 356/244; 356/246
(58) Field of Search .................. 422/50, 55, 58, 422/68.1, 73, 52, 100, 102, 104, 82.05, 82.06, 82.07, 82.08, 82.09, 82.11, 61, 63, 67, 81; 436/63, 66, 69, 70, 164, 165, 169, 172, 518, 2, 43, 174; 356/244, 246

(56) References Cited

U.S. PATENT DOCUMENTS

| | | | |
|---|---|---|---|
| 3,883,247 A | 5/1975 | Adams |
| 3,895,661 A | 7/1975 | Praglin et al. |
| 3,916,205 A | 10/1975 | Kleineman |
| 3,925,166 A | 12/1975 | Blume |
| 4,088,448 A | 5/1978 | Lilja et al. |
| 4,171,866 A | 10/1979 | Tolles |
| 4,427,294 A | 1/1984 | Nardo |
| 4,550,417 A | 10/1985 | Nunogaki et al. |
| 4,558,014 A | 12/1985 | Hirschfeld et al. |
| 4,790,640 A | 12/1988 | Nason |
| 4,853,210 A | 8/1989 | Kass |
| 4,950,455 A | 8/1990 | Smith |
| 5,028,529 A | 7/1991 | Ericcson |
| 5,122,284 A | 6/1992 | Braynin et al. |
| 5,132,097 A | 7/1992 | Van Deusen et al. |
| 5,223,219 A | 6/1993 | Subramanian et al. |
| 5,281,540 A | 1/1994 | Merkh et al. |
| 5,316,952 A | 5/1994 | Brimhall |
| 5,362,648 A | 11/1994 | Koreyasu et al. |
| 5,397,479 A | 3/1995 | Kass et al. |
| 5,427,959 A | 6/1995 | Nishimura et al. |

(List continued on next page.)

*Primary Examiner*—Jill Warden
*Assistant Examiner*—Brian Sines
(74) *Attorney, Agent, or Firm*—O'Shea, Getz + Kosakowski, P.C.

(57) ABSTRACT

An apparatus for analyzing a sample of biologic fluid quiescently residing within a chamber is provided. The apparatus includes a light source, a positioner, a mechanism for determining the volume of a sample field, and an image dissector. The light source is operable to illuminate a sample field of known, or ascertainable, area. The positioner is operable to selectively change the position of one of the chamber or the light source relative to the other, thereby permitting selective illumination of all regions of the sample. The mechanism for determining the volume of a sample field can determine the volume of a sample field illuminated by the light source. The image dissector is operable to convert an image of light passing through or emanating from the sample field into an electronic data format.

25 Claims, 4 Drawing Sheets

U.S. PATENT DOCUMENTS

| | | | |
|---|---|---|---|
| 5,482,829 A | 1/1996 | Kass et al. | |
| 5,541,064 A | * 7/1996 | Bacus et al. | 435/6 |
| 5,547,849 A | 8/1996 | Baer et al. | |
| 5,591,403 A | 1/1997 | Gavin et al. | |
| 5,608,519 A | 3/1997 | Gourley et al. | |
| 5,623,415 A | 4/1997 | O'Bryan et al. | |
| 5,646,046 A | 7/1997 | Fischer et al. | |
| 5,681,529 A | 10/1997 | Taguchi et al. | |
| 5,768,407 A | 6/1998 | Shen et al. | |
| 5,781,303 A | 7/1998 | Berndt | |
| 5,787,189 A | 7/1998 | Lee et al. | |
| 5,800,781 A | 9/1998 | Gavin et al. | |
| 5,837,546 A | * 11/1998 | Allen et al. | 436/169 |
| 5,879,628 A | 3/1999 | Ridgeway et al. | |
| 5,939,326 A | 8/1999 | Chupp et al. | |
| 5,948,686 A | 9/1999 | Wardlaw | |
| 6,004,821 A | 12/1999 | Levine et al. | |
| 6,022,734 A | 2/2000 | Wardlaw | |
| 6,106,778 A | 8/2000 | Oku et al. | |
| 6,251,615 B1 | * 6/2001 | Oberhardt | 435/7.21 |

* cited by examiner

APPARATUS FOR ANALYZING BIOLOGIC FLUIDS

This application is a divisional of, and claims priority under 35 U.S.C. §120 from U.S. patent application Ser. No. 09/255,673 filed Feb. 23, 1999, and claims the benefit of U.S. Provisional Patent application Ser. No. 60/077,210 filed Mar. 7, 1998.

BACKGROUND OF THE INVENTION

1. Technical Field

The present invention relates to apparatus for analyzing biologic fluid samples in general, and to apparatus capable of performing analyses in a variety of disciplines including hematology, biologic chemistry, immunochemistry, serology, immunology, and urinalysis in particular.

2. Background Information

Historically, biologic fluid samples such as whole blood, urine, cerebrospinal fluid, body cavity fluids, etc. have had their particulate or cellular contents evaluated by smearing a small undiluted amount of the fluid on a slide and evaluating that smear under a microscope. Reasonable results can be gained from such a smear, but the accuracy and reliability of the data depends largely on the technician's experience and technique. In addition, although biologic fluid sample smears are widely used for evaluation purposes, their labor-intensive nature makes them generally not favored for commercial applications.

Another known method for evaluating a biologic fluid sample involves diluting a volume of the sample, placing it within a chamber, and manually evaluating and enumerating the constituents within the diluted sample. Dilution is necessary if there is a high concentration of constituents within the sample, and for routine blood counts several different dilutions may be required because it is impractical to have counting chambers or apparatus which can examine variable volumes as a means to compensate for the disparities in constituent populations within the sample. In a sample of whole blood from a typical individual, for example, there are about $4.5 \times 10^6$ red blood cells (RBC's) per microliter ($\mu l$) of blood sample, but only about $0.25 \times 10^6$ of platelets and $0.007 \times 10^6$ white blood cells (WBC's) per $\mu l$ of blood sample. To determine a WBC count, the whole blood sample must be diluted within a range of about one part blood to twenty parts diluent (1:20) up to a dilution of approximately 1:256 depending upon the exact dilution technique used, and it is also generally necessary to selectively lyse the RBC's with one or more reagents. Lysing the RBC's effectively removes them from view so that the WBC's can be seen. To determine a platelet count, the blood sample must be diluted within a range of 1:100 to about 1:50,000. Platelet counts do not, however, require a lysis of the RBC's in the sample. A disadvantage of evaluating a whole blood sample in this manner is that the dilution process is time consuming and expensive. In addition, adding diluents to the whole blood sample increases the error probability within the sample data. Adding diluents also increases the quantity of waste material that must be disposed of upon completion of the test.

A modern method for evaluating a biologic fluid sample is impedance or optical flow cytometry. Flow cytometry involves circulating a diluted fluid sample through one or more small diameter orifices, each employing an impedance type or an optical type sensor that evaluates the constituents as they pass through the orifice in single file. Using the example of whole blood again, the sample must be diluted to mitigate the overwhelming number of the RBC's relative to the WBC's and platelets, and to provide adequate cell-to-cell spacing so that individual cells may be analyzed. Although more expedient and consistent than the above described methods, flow cytometers also possess numerous disadvantages. Some of those disadvantages stem from the plumbing required to carry the sample to, and the fluid controls necessary to control the fluid flow rate through, the sensor means. The precise control of this flow is essential to the cytometer's accurate operation. The plumbing within flow cytometers can and often does leak, potentially compromising the accuracy and the safety of the equipment. The fluid flow controls and dilution equipment require periodic recalibration. In fact, the need for recalibration illustrates the potential for inaccurate results and the undesirable operating costs that exist with many presently available hematology analyzers which use flow cytometers and/or impedance orifices. The volume of reagents required to satisfy large dilution ratios increases the operating cost initially by virtue of the reagent purchase price and subsequently because of the additional waste disposal costs.

Another modern method for evaluating biologic fluid samples is one that focuses on evaluating specific subtypes of WBC's. This method utilizes a cuvette having an internal chamber about 25 microns thick with one transparent panel. A laser beam of light passing through the transparent panel scans the cuvette for WBC's. Reagents added to the sample cause each WBC to fluoresce when excited by the laser beam. The fluorescing of the particular WBC's provides an indication that particular types of WBC's are present. Because the red blood cells form a partly obscuring layer in this method, they cannot themselves be enumerated or otherwise evaluated, nor can the platelets.

There are a multitude of methods for determining the presence of soluble constituents, such as chemical components, antibodies, etc., within a sample of biologic fluid such as urine, plasma, or serum. Most of the methods require dilution of the sample and the addition of one or more reagents to the sample. Other methods require a small, but carefully metered, drop of biologic fluid sample be added to a piece of reactive film. Different analytical instruments are usually required for each method of analysis, and those instruments are expensive not only in terms of initial capital cost but also in terms of the maintenance over the life of the various instruments, and the operator training necessary to properly staff the various instruments. The operator function can vary considerably from instrument to instrument, thereby increasing the complexity of the operator training and the potential for operator error. To date, because of the widely differing requirements of the various tests, there is not a single instrument platform which will perform cross-discipline tests, most especially tests of hematology, which require particle analysis, and tests of chemistry/immunochemistry or serology, which require quantitative light analysis.

What is needed is a method and an apparatus for evaluating a sample of substantially undiluted biologic fluid, one capable of providing accurate results, one that does not use a significant volume of reagent(s), one that does not require sample fluid flow during evaluation, one that can perform particulate component and chemical component analyses, and one that is cost-effective.

DISCLOSURE OF THE INVENTION

It is, therefore, an object of the present invention to provide an apparatus for analyzing biologic fluid samples that has the capacity to provide analytical data for a variety of disciplines including, but not limited to, hematology, biologic chemistry, immunochemistry, serology, immunology, urinalysis, immunoassay, antibiotic sensitivity, and bacterial growth.

It is another object of the present invention to provide a single apparatus for analyzing biologic fluid samples that has the capacity to perform a greater number of tests than can be done on any single presently available device.

It is another object of the present invention to provide an apparatus for analyzing biologic fluid samples that uses a quiescent sample, and thereby avoids the problems associated with devices utilizing fluid flow, particularly those utilizing fluid flow outside the sample chamber and those utilizing fluid flow during the analysis process.

It is another object of the present invention to provide an apparatus for analyzing biologic fluid samples that has the capacity to search a biologic fluid sample for an optimum region to perform a given test.

It is another object of the present invention to provide an apparatus for analyzing biologic fluid samples that has the capacity to determine the volume of a given sample field in a fluid sample chamber.

According to the present invention, an apparatus for analyzing a sample of biologic fluid quiescently residing within a chamber is provided. The apparatus includes a light source, a positioner, a means for determining the volume of a sample field, and an image dissector. The light source is operable to illuminate a sample field of known, or ascertainable, area. The positioner is operable to selectively change the position of one of the chamber or the light source relative to the other, thereby permitting selective illumination of all regions of the sample. The means for determining the volume of a sample field can determine the volume of a sample field illuminated by the light source. The image dissector is operable to convert an image of light passing through or emanating from the sample field into an electronic data format.

An advantage of the present invention is that the present invention apparatus for analyzing a sample of biologic fluid is substantially more versatile than any presently available apparatus capable of analyzing biologic fluid. For example, the present invention has utility in numerous fields including, but not limited to, hematology, biologic chemistry, immunochemistry, serology, immunology, urinalysis, immunoassays, antibiotic sensitivity, and bacterial growth. From an equipment standpoint, this versatility will give many medical offices and laboratories analytical capability that was realistically unavailable heretofore because of cost, space, manpower, training, etc. When testing a blood sample for anemia, for example, it is common to analyze the sample using hematological tests such as hemoglobin, hematocrit, and reticulocyte count, and also to analyze the sample using chemical tests to establish the presence and quantity of iron or ferritin and immunochemical tests such as B-12 and folate. Using presently available devices, the medical office or laboratory would typically rely on an impedance counter or flow system to determine the hematological parameters and a chemical analyzer or immunochemistry system to determine the other analytical parameters, any of which may not be readily available to the office or laboratory. The present invention apparatus, in contrast, can perform all of these tests. For those medical offices and laboratories that presently do have multiple discipline analysis capability, the present invention will substantially reduce equipment cost, space required, manpower and training.

The present invention can also, in most instances, increase the number of tests possible on one analysis device in a particular field. In the field of hematology, for example, the present invention can be programmed to perform analyses such as hematocrit and hemoglobin evaluation, white blood cell count, platelet count, red blood cell indices, red blood cell morphology, five-part differential, reticulocytes evaluation, white blood cell subset analyses, sedimentation rate (ESR), and sepsis detection. As far as is known, no single presently available analysis device can perform all of these analyses.

Another advantage of the present invention apparatus for analyzing a biologic sample is that it does not require substantial dilution or complex fluid handling apparatus. As stated in the Background of the Invention, analyzing whole blood in an impedance or optical flow cytometer has several drawbacks relating to the amount the sample must be diluted and the internal plumbing of the device. The present invention apparatus, on the other hand, requires relatively little or no dilution of the biologic sample, has no internal plumbing, and does not require external calibration. A person of skill in the art will recognize that it is a significant advantage to provide an apparatus with increased reliability. Specifically, the present invention's lack of plumbing eliminates the possibility of downtime attributable to plumbing leaks or that due to a sensor being miscalibrated. The present invention also avoids the expensive service contracts associated with many flow cytometers. Perhaps most importantly, the lack of need for any external calibration removes a large source of potential errors and considerable operational complexity.

Another advantage of the present invention apparatus for analyzing a biologic sample is that it provides faster results for a complete set of tests. In many cases, faster test results mean better patient care because a patient may be evaluated with the results of the tests in hand, rather than the current practice of releasing the patient and requiring a repeat visit if unusual results are encountered. Faster test results also enable the medical office or laboratory to process more test samples in a given period of time, thereby increasing the number of patients that can helped and the revenue stream that emanates therefrom.

Another advantage of the present invention is its ability to search a biologic fluid sample for an optimum region(s) to perform a given test. One of the problems common to analyzing biologic samples is that the concentration of constituents within the sample can vary dramatically. Presently available analysis apparatus accounts for the spectrum of constituent concentrations by performing several test iterations. For example if the constituent population within a particular sample is too great, a second iteration of sample must be created by dilution to decrease the number of constituents in a given volume, or vice-versa. This dilution process increases the analysis time and cost, and the probability of error in the analysis. The present invention, in contrast, avoids multiple dilutions by using a biologic fluid container which can segregate constituents and the concentrations of constituents within a chamber, and by having means to know which constituents are where and in what concentration within the chamber for a given analysis. In addition, the present invention is capable of evaluating regions within the sample contained within the chamber comparatively to find a sample region having optimum characteristics for the test(s) at hand. In those situations where it is desirable to evaluate the sample statistically, the present invention can be programmed to evaluate a plurality of regions containing acceptable characteristics and that data collectively analyzed.

Another advantage of the present invention is that it provides a safe means to handle biologic samples. The present invention apparatus includes means for safely handling biologic fluid samples during analysis. Risks associated with handling and disposing of biologic fluid samples are consequently minimized.

These and other objects, features and advantages of the present invention will become apparent in light of the detailed description of the best mode embodiment thereof, as illustrated in the accompanying drawings.

BEST MODE FOR CARRYING OUT THE INVENTION

Figure 1:
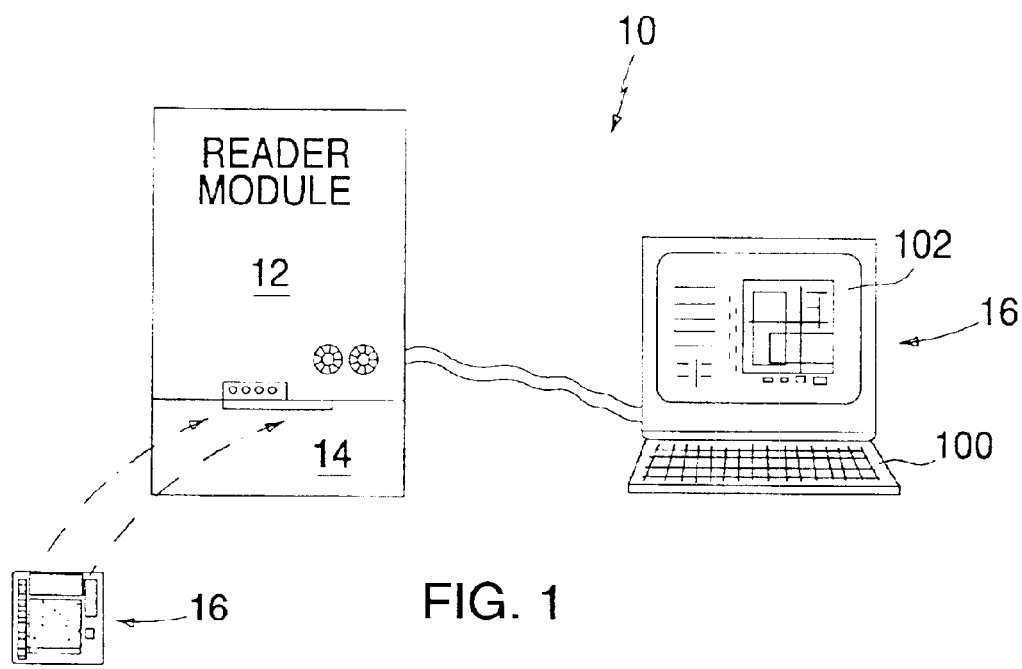
FIG. 1 is a diagrammatic view of the present invention apparatus for analyzing a sample of biologic fluid quiescently residing within a chamber.
Figure 2:
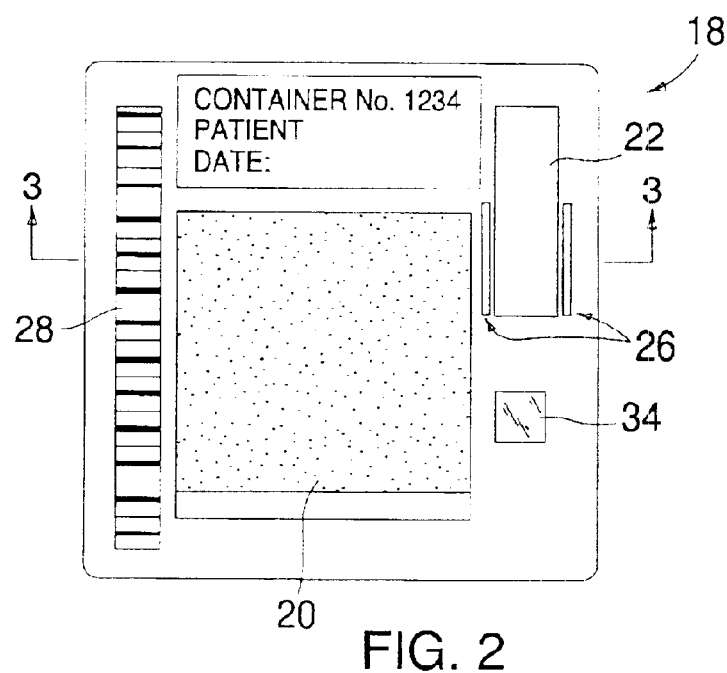
FIG. 2 is a diagrammatic view of a container for holding a biologic fluid sample for analysis.

Referring to FIGS. 1 and 2, the apparatus 10 for analyzing a sample of biologic fluid quiescently residing within a chamber includes a Reader Module 12, a Sample Transport Module 14, and a Programmable Analyzer 16. For purposes of this disclosure the terms "analyze" and "analysis" shall be defined as any examination or evaluation of the fluid sample, including but not limited to, the examination of constituents within the sample. The present invention apparatus 10 is preferably used with a particular container 18 for holding a biologic fluid sample for analysis, which is the subject of U.S. Pat. No. 6,723,290 and is incorporated herein by reference. Briefly described, the container 18 includes at least one chamber 20, a reservoir 22, a channel 24 (FIG. 3) connecting the chamber 20 and the reservoir 22, a valve 26 functionally disposed between the reservoir 22 and the chamber 20, and a label 28. The chamber 20 (see FIG. 3) includes a first wall 30 and a transparent second wall 32. In some embodiments, the first wall 30 is also transparent. Fluid sample residing within the chamber 20 may be imaged through one or both transparent walls 30,32. The container 18 further includes one or more features operable to enable the analysis of the biologic fluid. At least one of the features is spatially located within the chamber 20 at a known spatial location. Features may include physical characteristics (e.g., a particular through-plane thickness at a known spatial location), geometric characteristics (e.g., an object of known volume located at a known spatial location), reagents disposed within the reservoir 22, or a colorant calibration pad 34, etc. The container label 28 stores information that is communicated to the apparatus 10 through a label reader 38 (FIG. 4).

I. The Reader Module

Figure 4:
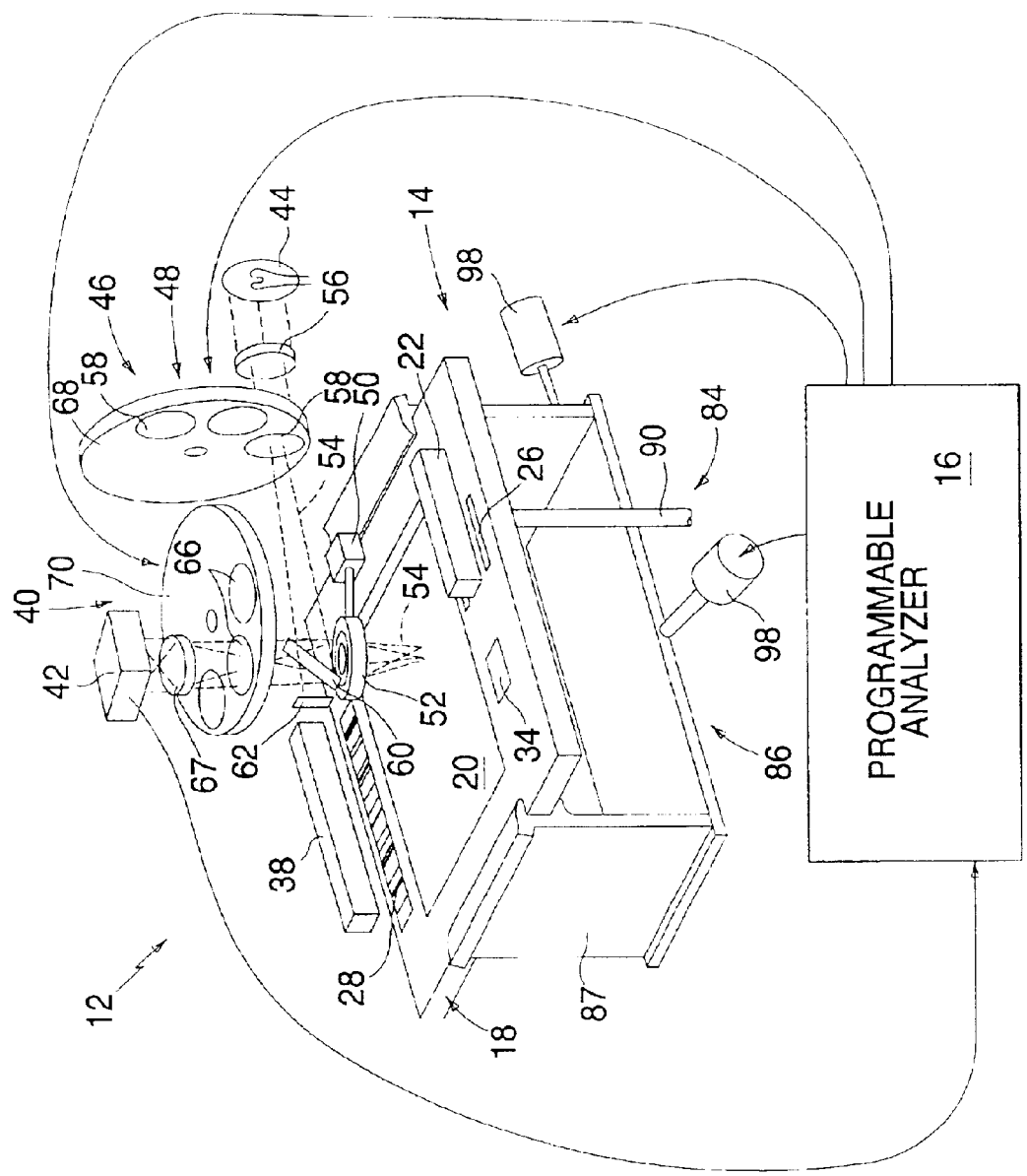
FIG. 4 is a diagrammatic view of an embodiment of the present invention Reader Module which utilizes fluorescence to produce an image.
Figure 5:
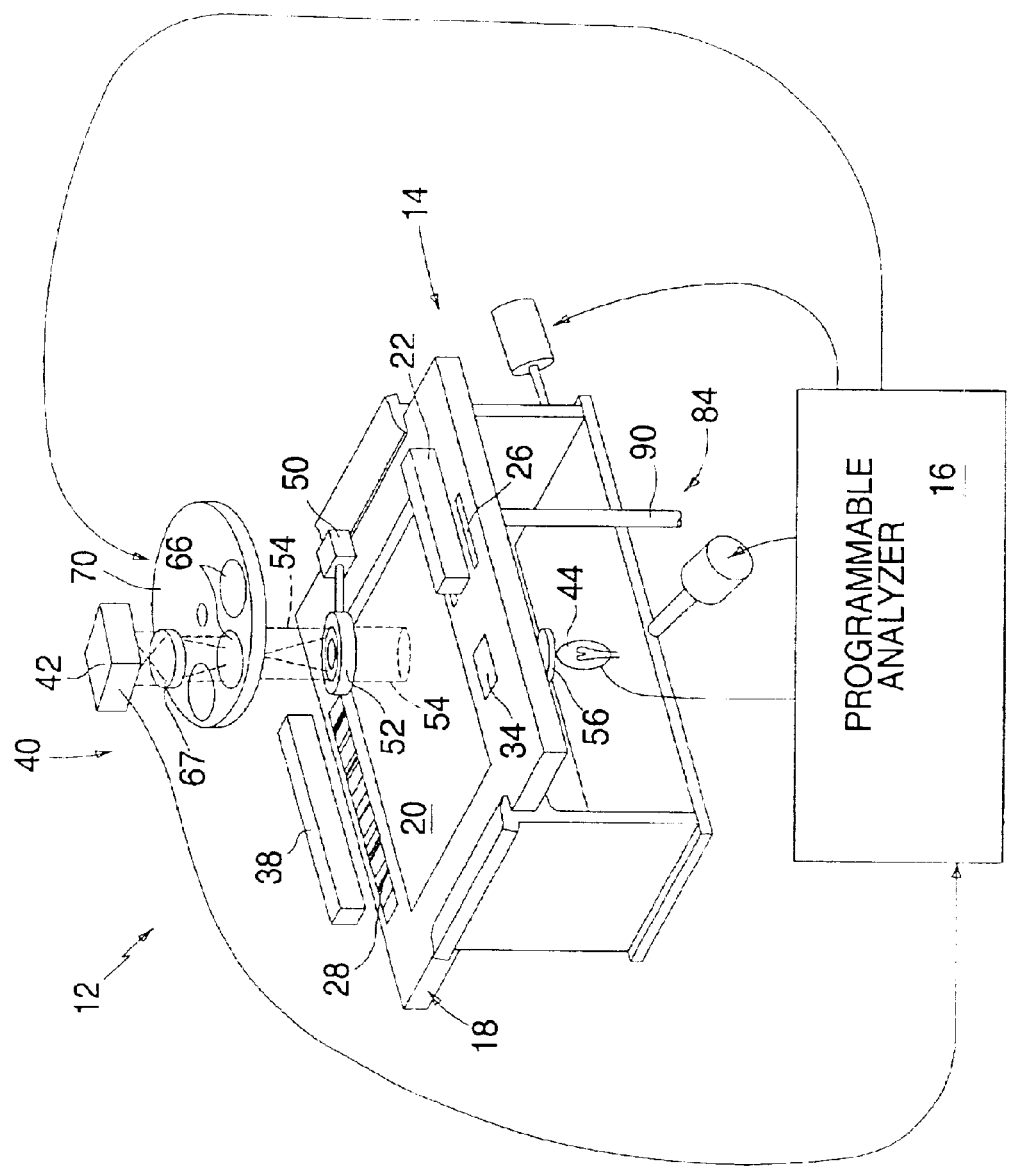
FIG. 5 is a diagrammatic view of another embodiment of the present invention Reader Module which utilizes fluorescence to produce an image.

Referring to FIGS. 4 and 5, the Reader Module 12 includes the aforementioned label reader 38, a field illuminator 40, means for determining the volume of a field of the sample, and an image dissector 42. The container label reader 38 is a mechanism for transferring information from the container 18 to the apparatus 10. A practical example of a container label 28 is one which is machine readable and one which is capable of communicating information including, but not limited to: 1) the type of analysis(es) to be performed; 2) information concerning the type of features, and the coordinate addresses of those features located within the sample chamber 20; 3) reagent information; 4) lot information; 5) calibration data; etc. If, for example, the label 28 is a magnetic strip or a bar code strip, then the label reader 38 is a device capable of reading the magnetic strip, the bar code strip, etc. In some instances, it may be possible to store and extract all of the necessary information from the label 28 itself. In other instances where the quantity of information to be communicated is considerable, however, it may be more practical to have the label 28 direct the apparatus 10 to a data file stored within the Programmable Analyzer 16 or stored remotely that contains all the appropriate information. Remotely stored data files can be accessed via modem, dedicated telecommunications line, the internet, wide area network, or other telecommunication means. The label 28 may also be a physical feature such as a tab whose position is interpretable by the label reader 38; e.g., different tab positions relate to different data files.

The field illuminator 40 includes a light source 44, objective optics 46, and preferably a light filtering means 48. The light source 44 selectively produces light throughout a wavelength range broad enough to be useful for a plurality of analyses (e.g., approximately 340 nm to 670 nm), from a mechanism such as a fifty watt zenon arc lamp or tungsten halogen lamp, or a pulsatile source of about ten joules. Other light sources may be used alternatively and the wavelength range of the light source may vary depending upon the application. Alternatively, a light source 44 which selectively produces particular wavelengths of light within the above identified range, or a plurality of light sources 44 each of which produces particular wavelengths within the above identified range, may be used. The objective optics 46 include a focusing mechanism 50 for adjusting the position of an objective lens 52 relative to the container 18 (or vice versa). The objective lens 52 focuses light emanating from the light source 44 into a light beam 54 which, in turn, is directed into the sample quiescently residing within the chamber 20. The light beam directed into the sample is of sufficient area to illuminate at least one imaged field of the sample. The sample field is defined by the cross-sectional area of the sample image which impinges on the image dissector 42, or a portion thereof, as directed by the objective optics 46 and any intervening field stops. The light filtering means 48, when included, is used to improve the quality and/or clarity of the desired sample image for a given test or to allow a precise quantitative measurement of light energy emitted from, or passing through, relevant portions of the sample. If the light source 44 is capable of selectively producing particular wavelengths, it may be possible to omit the light filtering means 48.

The preferred embodiment of the field illuminator 40 varies depend upon the principle used to produce the image. Referring to FIG. 4, a first embodiment of the field illuminator 40 utilizes fluorescence to produce an image. The first embodiment includes a flash tube type light source 44, optics 46, and a light filtering means 48, the latter of two which include a first lens 56, a light source excitation filter 58 ("LSE" filter), a light diverting prism 60, a reference detector 62, an objective lens 52, a sample emission filter 66 ("SE" filter), a second lens 67, and a focusing mechanism 50. The light diverting prism 60 may be a polarizing prism, a dichroic beam splitter, or a half-silvered mirror or prism. The first lens 56 collects light emanating from the flash tube, or alternate source of illumination, and directs it through the LSE filter 58. The LSE filter 58 allows light of a predetermined wavelength(s) to pass through (this function can also be described as blocking all but predetermined wavelengths from passing through) and continue on where it strikes the light diverting prism 60. A portion of the light then passes through the light diverting prism 60 and strikes the reference detector 62 positioned adjacent the light diverting prism 60. Feedback from the reference detector 62 allows the filtered excitation light energy to be measured. Since fluorescence emission is directly proportional to the energy of the fluorescence excitation, any variations in the excitation light energy, as measured by the reference detector 62, can be used to either adjust the intensity of the emission source or to calculate a corrected emission energy. Another portion of the light entering the light diverting prism 60 is reflected approximately ninety (90) degrees downward through the objective lens 52 and subsequently into the container chamber 20 where the biologic fluid sample quiescently resides. The objective lens 52 is attached to the focusing mechanism 50 that enables the distance between the objective lens 52 and the chamber 20 to be varied as necessary for focusing purposes. A controllable stepper motor arranged to change the focal distance between the objective lens 52 and the container 18 is an example of a focusing mechanism 50. Typically, the objective lens 52 is moved relative to the container 18, or vice versa, but alternative methods may be used. The wavelengths of light passing through the LSE filter 58 and the objective lens 52 subsequently enter the sample, causing material within the sample bearing a chosen colorant to fluoresce and emit light of a particular wavelength. That emitted light passes back through the objective lens 52, through the light diverting prism 60, and then through the SE filter 66. The SE filter 66 blocks all but (or passes) select wavelengths of light. Those wavelengths of light subsequently pass through the second lens 67 and encounter the image dissector 42. The SE filter 66 is preferably a tunable liquid crystal display (LCD) filter.

If there is more than one LSE filter 58, the LSE filters 58 are attached to a first filter wheel 68. The first filter wheel 68 is synchronized with the light source 44 such that the light source 44 is selectively actuated when the desired LSE filter 58 is positioned in the path of the light beam 54 as described above. Likewise, if there is more than one SE filter 66, the SE filters 66 are attached to a second filter wheel 70. The second filter wheel 70 is synchronized with the light source 44 such that the light source 44 is selectively actuated when the desired SE filter 66 is positioned in the path of the light beam 54. If there is more than one LSE filter 58 and more than one SE filter 66, then the first and second filter wheels 68,70 and the light source 44 are synchronized such that the light source 44 is selectively actuated when the desired LSE and SE filters 58,66 are positioned in the path of the light beam 54.

Referring to FIG. 5, the second embodiment of the field illuminator 40 utilizes transmittance to produce an image. In the second embodiment of the field illuminator 40, measurement of the light transmission properties of the sample is accomplished by positioning a white light source 44 and a first lens 56 under the sample residing within the chamber 20 and directing the light through the chamber first wall 30 (which is transparent in this embodiment), the sample, the chamber second wall 32, the objective lens 52, the SE filter 66, the second lens 67, and thereafter to the image dissector 42. The transmittance light is intermittently energized as transmittance measurements are required. The light source 44 may be pulsatile, such as from a flash tube, or it may be an incandescent bulb with a means for selectively exposing the sample to the light such as a shutter, or an electronic switch that extinguishes the light entirely.

The preferred image dissector 42 is a charge couple device (CCD) capable of providing at least eight bits of resolution and preferably twelve bits of resolution per pixel. The image dissector 42 converts an image of the light passing through the SE filter 66 into an electronic data format which can be seen and/or interpreted in real-time or at a subsequent time using a data file version of the image. The image can be interpreted manually by a technician, or with the use of analytical software. An image dissector 42 other than a CCD may be used to convert the image of light into an electronic data format alternatively.

Figure 6:
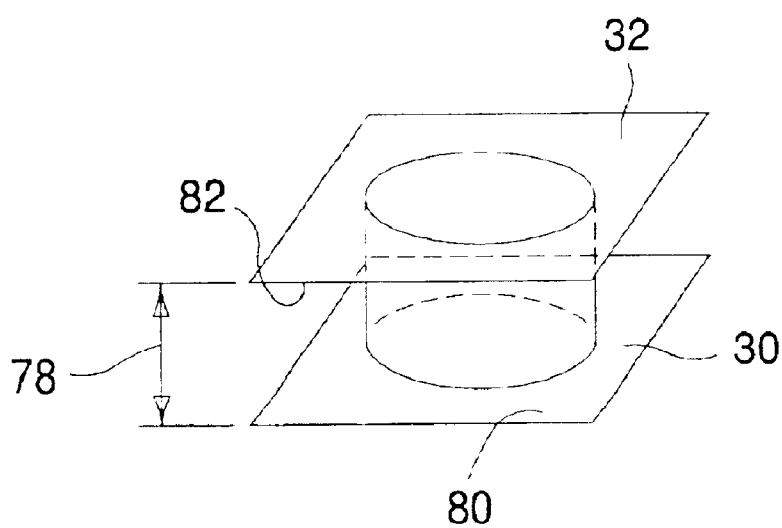
FIG. 6 is a diagrammatic illustration of a sample field between a first chamber wall and a second chamber wall.

Referring to FIG. 6, as used herein the term "volume" for volume of the field can mean the volume itself, or can refer to the through-plane thickness 78 of the imaged field because one can be readily determined from the other given the cross-sectional area of the field. As used herein, the term "through-plane thickness" refers to a line of sight that corresponds to the shortest distance 78 between the interior chamber surface 80 of the first wall 30 and the interior chamber surface 82 of the second wall 32.

Figure 3:
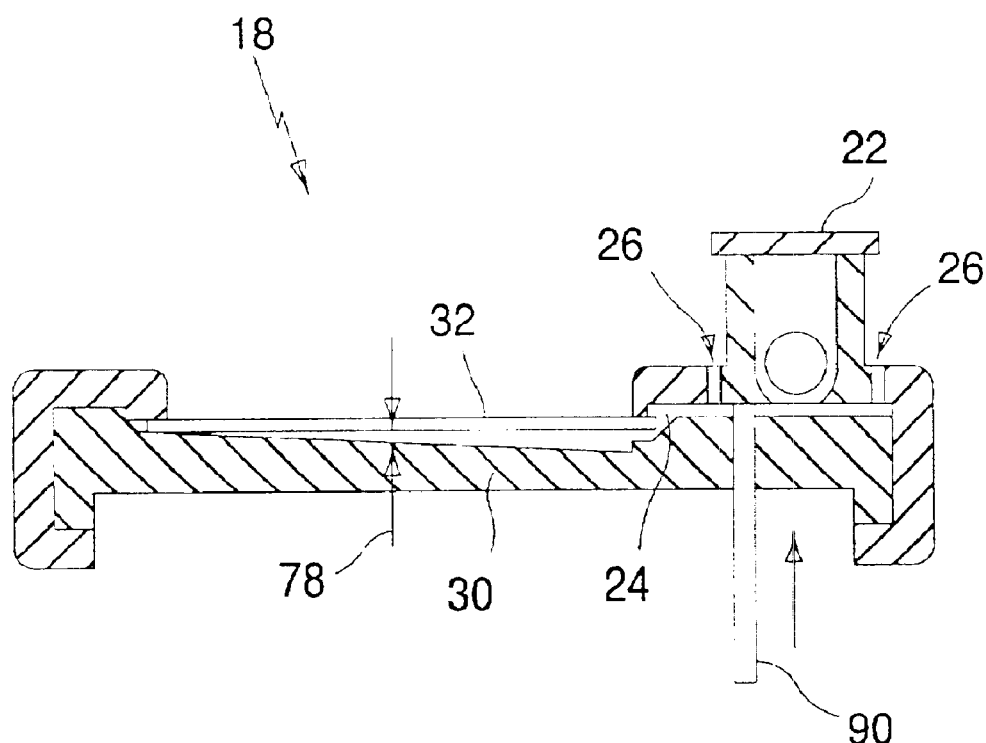
FIG. 3 is a cross-sectional view of the container shown in FIG. 2.

Referring to FIGS. 3 and 4, in a first embodiment of the means for determining the volume of one or more fields within the sample, the label reader 38 reads the container label 28 which communicates the chamber 20 geometry to the apparatus 10 and with that information the volume of the field can be determined. For example, if the label 28 provides the slope values of the chamber first wall 30 and second wall 32 and a through-plane thickness 78 value at a known spatial location, the volume of a field at any position within the chamber 20 can be determined provided the slope values are constant for both walls 30,32 for the entire chamber 20.

In a second embodiment of the means for determining the volume of one or more select fields within the sample, the volume is determined by sensing the colorant signal from a sample field of unknown volume containing fluid sample having a known colorant concentration. The colorant signal magnitude to colorant concentration ratio is communicated to the apparatus 10 through the container label 28 and label reader 38. As used within this specification, the term colorant is defined as any reagent that produces a sensible signal by fluorescent emission, or by absorption of light at a specific wavelength, that can be quantified by the apparatus 10. The signal magnitude to colorant concentration may also be determined by comparison with a second known material such as a pad 34 of material with stable characteristics which is referenced by the apparatus 10 and used to calibrate the response of the colorant.

In a third embodiment of the means for determining the volume of one or more select fields, the volume is determined by comparing colorant signal from at least two sample fields. The first and second sample fields contain colorant of unknown concentration uniformly distributed within the fluid sample. The first field, referred to here as the calibration field contains a geometric characteristic-type feature of known height or volume. Examples of geometric characteristics include a step, a cavity, or a protuberance of known height or volume within one or both walls, or an object of known volume. The volume or height of the geometric characteristic is provided to the Programmable Analyzer 16 through the container label 28 and label reader 38. The change in sensible signal due to the displacement of colorant by the known geometric characteristic in the calibration field is measured through the field illuminator 40, and a calibration value of change in sensible signal per volume is calculated by the Programmable Analyzer 16 and stored. To determine the volume of the second, or unknown field, the Programmable Analyzer 16 takes the signal measured from the second field and multiplies it by the signal/volume ratio of the calibration field to arrive at a volume for the second field. This method of volume determination is further described in U.S. Pat. No. 6,127,184.

In a fourth embodiment of the means for determining the volume of one or more select fields, the volume of the field(s) is determined using interferometric techniques to measure the through-plane thickness. The hardware necessary to perform the interferometric techniques includes a monochromatic light source and a beamsplitter which operate together to form interference patterns, where the number of observable interference fringes is related to the separation of the chamber walls 30,32.

In a fifth embodiment of the means for determining the volume of one or more select fields, the container chamber 30 includes specular surfaces on which a virtual reflected image may be detected by the apparatus 10. The specular surfaces are the two wall surfaces 80,82 in contact with the biologic fluid, or the outer surfaces if the wall thicknesses are known. The apparatus 10 detects the virtual reflected image on one of the specular surfaces and then refocuses on the virtual reflected image formed on the other specular surface. The distance that the field illuminator optics 46 move between the two images is the through-plane thickness 78 of the chamber 20 in the particular field. A sixth and related embodiment is the use of identifiable patterns on each of the two chamber surfaces 80,82, where these patterns are used as focal targets, as opposed to the virtual images used in the fifth embodiment, and are disclosed in U.S. Pat. Nos. 5,781,303 and 6,127,184.

II. The Sample Transport Module:

The Sample Transport Module 14 includes a mechanism 84 for transferring biologic fluid sample from the container reservoir 22 to the container chamber 20 and a container positioner 86. When the preferred container 18 is used, the mechanism 84 includes a valve actuator, for example rod 90, that selectively actuates the container valve 26 to transfer fluid sample from the container reservoir 22 to the container chamber 20. The mechanism 84 for transferring fluid sample from the reservoir to the chamber may be automated or manual and in all cases is sufficient to operate the valve 26, if any, disposed in the container 18. For those tests which are not time related, the biologic fluid sample may be placed directly into the container chamber 20 thereby obviating the need for a reservoir 22, a valve 26, and a valve actuator 90.

In all of its embodiments, the positioner 86 is operable to selectively change the position of one of the container 18 or the field illuminator 40 relative to the other of the container 18 or the field illuminator 40, such that all regions of the sample within the chamber 20 can be selectively illuminated and imaged. The container 18 can be initially located relative to the field illuminator 40 by means of a recognizable feature (e.g. a notch in the container 18), such that once the field illuminator 40 locates the recognizable feature, all other features within the chamber 20 can be accessed by virtue of their coordinate address (i.e., known spatial location). In a simplistic embodiment, the positioner 86 might include a pair of thumb wheels geared to a tray 87 (or to the field illuminator 40), such that the tray 87 (or the field illuminator 40) can be moved in a plane by rotating the thumb wheels, in a manner similar to that of a microscope stage. In a second embodiment, the positioner 86 includes electromechanical actuators 98 for moving the disposable container 18 in the plane (e.g., the x-y plane) relative to the imaged field (or vice versa). The actuators 98 may be any electromechanical device that can accurately and repeatably position the container 18 and hold that position until directed otherwise. For those analyses that require mixing of the biologic sample and a reagent, the actuators 98 may also be capable of moving the container 18 in a manner that causes the sample and reagent to mix within the reservoir 22.

III. The Programmable Analyzer

Referring to FIGS. 1 and 4, as stated earlier, the Programmable Analyzer 16 is described herein as a stand alone device that is in communication with the Reader Module 12 and the Sample Transport Module 14. The Programmable Analyzer 16 could, alternatively, be packaged with the Reader Module 12 and Sample Transport Module 14 in a single device.

The Programmable Analyzer includes a central processing unit (CPU) and hardware connecting the Reader Module 12, Sample Transport Module 14, and the Programmable Analyzer 16 together. Software programmed into the CPU (or remotely accessible by the CPU) provides instruction sets, hereinafter referred to as analysis algorithms, that detail all the steps necessary to perform a variety of analyses. Simplistic instruction sets may alternatively be provided directly to the Programmable Analyzer 16 through the container label 28 and label reader 38. The Programmable Analyzer 16 preferably further includes a keyboard/keypad type input device 100 and a monitor type display device 102. A variety of acceptable keyboards/keypads and monitors are commercially available and therefore will not be described further. The CPU is programmed to control the Reader Module 12 and the Sample Transport Module 14, directing them to perform tasks according to the analysis algorithm at hand. The CPU is also programmed to receive and manipulate the electronic data format of the fluid sample image (referred to hereinafter generally as "data") produced by the image dissector 42. The analysis algorithms and/or input from the operator and/or container label 28 provide the instructions for manipulating the data into a useful output.

The CPU's programming reflects the apparatus's 10 level of automation. In the case of the simplistic embodiment of the positioner 86, no positioner programming is provided because manually operated thumb wheels are used in lieu of automation. Likewise, the mechanism 84 for transferring biologic sample from the container reservoir 22 to the container chamber 20 may also be manually operated. In an automated embodiment, programming stored within the CPU or remotely accessed by the CPU (and/or input from the keyboard 100) enables the CPU, for example, to control the label reader 38 to extract information from the container label 28, to transfer biologic sample from the container reservoir 22 to the container chamber 20, and to control movement of the container 18 relative to the Reader Module 12 (or vice versa).

The analysis algorithms programmed into the CPU help give the present invention apparatus its versatility and ability to perform analyses in a variety of disciplines. The algorithms are constructed to utilize the features of the container 18 as well as the capabilities of the apparatus 10 such as the Reader Module's 12 ability to determine the volume of one or more select sample fields and the Sample Transport Module's 14 ability to move the container 18 to permit access to any sample field. As a general overview of how such algorithms would work, when the container 18 is loaded into the apparatus 10, the container label 28 is read thereby providing the Programmable Analyzer 16 sufficient information to determine what test(s) is requested and the information necessary to perform that test. The Programmable Analyzer 16 is programmed to use the label information to access the appropriate analysis algorithm and in some instances data files stored within the Analyzer 16 (or stored remotely) as well. The analysis algorithm, in turn, provides the step by step instructions necessary to direct the Sample Transport Module 14 and the Reader Module 12, and any other functions necessary in the performance of the test.

The instructions may direct the Reader Module 12 to actuate the container valve 26 thereby transferring the fluid sample from the reservoir 22 to the chamber 20. For those analyses that are timed, the valve actuation may be used to initiate the time period. The Reader Module 12 may also be used to visually monitor the chamber 20 to determine if or when an optimum quantity of sample has reached the chamber 20. The instructions can also direct the Reader Module 12, based on information provided through the container label 28, to use particular filters 58,66 appropriate for particular wavelengths, or to move the container 18 to particular positions to provide the Reader Module 12 access to particular fields, etc. When the test at hand calls for a chemical measurement, for example, the analytical algorithm identified through the label 28 will call for the measurements necessary to determine the optical density of the field. The concentration of the analyte can subsequently be calculated by the Programmable Analyzer 16 using an analysis algorithm that uses calibration data communicated through the container label 28. For hematology analyses, on the other hand, an analysis algorithm may direct that a field be searched for images of a particular cell type for enumeration or evaluation purposes. The algorithm may direct that a single, most optimal field be considered, or most preferably that multiple fields be considered and the results be statistically analyzed to obtain a final statistically acceptable result. At one or more points during the analyses, the volume of the sample field may be determined, if required for the analysis, and that data used in the final results calculation.

As stated above, the considerable utility of the apparatus 10 enables a wide variety of analyses to be performed of a single sample, using a single analytical container 18. The detailed examples given below are offered so that a complete appreciation of the present invention apparatus may be gained.

EXAMPLE I

Hematological Analyses

Referring to FIG. 4, to enable an analysis of white blood cells (WBC's) within an anticoagulated whole blood sample, a container 18 having approximately 0.8 micrograms ($\mu$g) of a sensible colorant and 50 $\mu$l of anticoagulated whole blood disposed within its reservoir 22 is inserted into the Sample Transport Module 14. Prior to insertion, the operator may gently shake the container 18 to ensure uniform mixing of the colorant and the fluid sample. The label reader 38 disposed within the Reader Module 14 reads the container label 28 and transfers the information contained within the label 28 to the Programmable Analyzer 16. In this example, the information identifies one or more specific analysis algorithms to be used and a plurality of container features operable to enable the analysis of the biologic fluid sample. Those features include identifying the anticoagulating agent as EDTA, the sensible colorant as a fluorescent highlighting supravital stain such as acridine orange (or basic orange-21 or the like), and physical characteristics of the container chamber 20 and the spatial locations of those physical characteristics within the chamber 20. For this particular analysis, only the second wall 32 of the container chamber 20 need be transparent since a fluorescent stain is being used. In all cases, it is the features of the container 18 and the capabilities of the apparatus 10 to utilize those features that enables the apparatus 10 to perform a plurality of tests on a single sample.

Referring to FIGS. 3 and 4, the Programmable Analyzer 16 next directs the rod 90 within the Reader Module 12 to actuate the valve 26 within the container 18 and thereby release the sample and colorant mixture into the chamber 20. Once the sample is distributed within the chamber 20, the sample resides quiescently during the analysis. The only sample motion within the chamber 20 will possibly be Brownian motion of the sample's formed constituents, and that motion is non-disabling for the present invention. Using the information provided through the container label 28, the analysis algorithm directs the positioner 86 to move the container 18 to a position where the field illuminator 40 is aligned with a first region of the chamber 20, and in particular with one of a plurality of fields having a through-plane thickness 78 of approximately twenty microns. The intra-chamber spatial location of each of these fields is known and communicated to the Programmable Analyzer 16 through the label 28. The chamber through-plane thickness 78 of approximately twenty microns is chosen for a couple of reasons. First, an evaluation volume of 0.02 $\mu$l, (formed by a particular sample field having a cross-sectional area of one millimeter (mm) and a through-plane thickness 78 of twenty microns) typically contains 50–200 WBC's which is a favorable quantity for evaluative purposes. The cross-sectional area referred to is the area of the sample imaged by the field illuminator 40 as described above. Second, a through-plane thickness 78 of twenty microns provides an optimal chamber 20 for rouleaux and lacunae formation.

If the sample is imaged by the apparatus 10 immediately after the sample has been inserted into the chamber 20, the sample will appear opaque when examined with the epiilluminated fluorescence and will not be favorable for analysis. The opaque appearance is caused by the red blood cells (RBC's), which form an overlapping mass prior to the formation of the rouleaux. To avoid an undesirable opaque image, the analysis algorithm stored within the Programmable Analyzer 16 provides a timing function wherein operation of the field illuminator 40 is delayed for a period of approximately thirty (30) seconds after the sample has been introduced into the chamber 20. During that time, the Programmable Analyzer 16 may position the appropriate SE or LSE filters 58,66 if any, within the path of the light beam 54 within the field illuminator 40. After the delay, light selectively produced from the light source 44 and filtered within the field illuminator 40 is directed into a sample field within the chamber 20. The light passing into the sample causes the colorant within the sample to fluoresce and emit light of a particular wavelength. The emitted light then passes through the field illuminator 40 and into the image dissector 42 where it is converted into an electronic format in real time.

The electronic format of the emitted image, which can be shown real-time on the monitor 102, will show that after lying substantially motionless for approximately thirty (30) seconds within the chamber 20, the RBC's will have spontaneously clustered into a plurality of rouleaux separated by lacunae. It is in the lacunae where whole blood sample constituents other than RBC's (e.g., WBC's and platelets)

can be found and evaluated. Using 0.02 µl sample fields keeps the number of WBC's in each field reasonable (a normal whole blood sample contains approximately 7,000 WBC's per µl of sample; a 0.02 µl sample of normal whole blood contains approximately 140 WBC's). A number of fields within the first region are evaluated until a statistically sufficient number of cells are counted, which in practice is approximately 1000 cells.

Referring to FIGS. 1 and 4, in the event it is determined through the analysis algorithm that the sample WBC population within the fields of the first region is too low to obtain statistically accurate information, the Programmable Analyzer 16 directs the Reader Module 12 to perform the evaluation process again, this time in a second region of the chamber 20 having a plurality of fields with a through-plane thickness 78 slightly larger than twenty microns. The larger volume of the fields within the second region are more apt to have a sample with a statistically acceptable population of WBC's. Likewise, if the WBC population within the sample is too high to obtain statistically accurate information from the fields within the first region of the chamber 20, the Programmable Analyzer 16 directs the Reader Module 12 to perform the evaluation process again, this time in a third region of the chamber 20 having a plurality of fields with a through-plane thickness 78 slightly smaller than twenty microns and consequent lesser volume. In either case, the intra-chamber spatial locations of the fields in either region are known and communicated to the Programmable Analyzer 16 through the label 28. The above described iterative process for finding a region possessing an optimum number of constituent WBC's within the substantially undiluted anticoagulated whole blood sample is an example of the apparatus's capacity to produce optimum results for a given analysis.

If additional WBC information is sought, the WBC's (lymphocytes, granulocytes, monocytes, etc.) can be analyzed within the sample using the image dissector 42 of the Reader Module 12, for example, alone or with analysis software. A differential count could be determined from the data collected. These and other hematologic tests are more completely described in U.S. patent application Ser. No. 09/249,721 and U.S. Pat. No. 5,948,686.

EXAMPLE II

Chemical Analyses

Referring to FIGS. 1 and 4, a complete blood count requires that the RBC's be evaluated for hemoglobin content using a chemical analysis. The operator deposits the whole blood sample into the container reservoir 22 and gently shakes the container 18 to ensure uniform mixing of the sample and a colorant previously deposited in the reservoir 22, and inserts the container 18 into the Reader Module 12. The label reader 38 reads the container label 28 and transfers the information contained within the label 28 to the Programmable Analyzer 16. Similar to the process described above, the label-provided information identifies a plurality of analysis algorithms and a plurality of container features operable to enable the analysis of the biologic fluid sample. In this example, the container features include lysing and stabilizing reagents and their spatial location within a chamber 20, the colorant deposited in the reservoir, and physical characteristics of the chamber 20 at known spatial locations. In a first embodiment, the container 18 includes a first chamber and a second chamber, both in fluid communication with the reservoir 22. The hemoglobin evaluation is performed in the first chamber and the remainder of the complete blood count tests are performed in the second chamber. In a second embodiment, all of the tests necessary for the complete blood count, including the hemoglobin evaluation, are done in a single chamber 20. The lysing reagent is used to break down RBC's within the sample and thereby release the hemoglobin stored within the RBC'S. The stabilizer reagent is used to increase the reliability of the hemoglobin evaluation.

After the container 18 is loaded in the Reader Module 12, the Programmable Analyzer 16 directs the rod 90 to actuate the container valve 26 and thereby release the sample and colorant mixture into the first chamber. At the same time the valve 26 is actuated, the analysis algorithm stored within the Programmable Analyzer 16 starts an internal timer, and the hemoglobin analysis is performed after one or more predetermined intervals of time. The analysis algorithm for the hemoglobin evaluation operates in a manner similar to that described above in the hematology example where the Programmable Analyzer 16 positions the appropriate SE or LSE filters 58,66 if any, within the path of the light beam 54 within the field illuminator 40, and light beam 54 selectively produced from the light source 44 and filtered within the field illuminator 40 is directed into the sample quiescently residing within the first chamber forming a field having an imaged area, etc. The light emitted from the colorant within the sample passes back through the field illuminator 40 and into the image dissector 42 where it is converted into an electronic format in real time, and the optical density of the hemoglobin in the first chamber is measured and the hemoglobin concentration is calculated. The remaining analyses associated with a complete blood count are performed in the second chamber.

In the second embodiment where all of the complete blood count analyses are performed in a single chamber 20, the portion of the biologic fluid sample used for the hemoglobin evaluation is contiguous with remaining portion of the fluid sample. The fluid sample portion devoted to the hemoglobin evaluation is preferably oriented toward one side of the chamber 20, however, to minimize potential mixing of the lysing agent with the remaining portion of the fluid sample. The coordinate addresses (i.e., spatial locations) of the hemoglobin evaluation reagents and the chamber region where the evaluation is best performed are communicated to the Programmable Analyzer 16 via the label 28. The chamber through-plane thickness 78 in the hemoglobin evaluation region is small enough such that vertical diffusion (and ultimate equilibrium) of the chemical reagents within the biologic fluid sample occurs at a much faster rate than lateral diffusion, thereby preventing the lateral diffusion of the reagent and possible interferences with the analyses to be performed.

EXAMPLE III

Urinalysis

Referring to FIGS. 1 and 4, a complete urinalysis requires a chemical analysis and a particulate analysis of the urine sample. The operator places a urine sample within the reservoir 22 of the container 18 and the container 18 is installed within the Reader Module 12. The label reader 38 reads the container label 28 and passes the information contained therein to the Programmable Analyzer 16. The information from the label 28 identifies a plurality of analysis algorithms and container features operable to enable the analysis of the biologic fluid sample, and like the hemoglobin example above, the analyses may be performed in a single chamber 20 or in a plurality of chambers. In this example, the label 28 provides information that the container features include colorant disposed in the container reservoir 22, one or more chemical reagents disposed at known spatial locations within a chamber 20 to colorometrically relate information concerning the specific gravity, pH, glucose, and ketones within the urine sample after a given period of time, and physical characteristics of the chamber 20 at known spatial locations that enable detection, evaluation, and/or enumeration of particles within the urine sample. The physical characteristics of the chamber 20 may, for example, be similar to those described above for the evaluation of WBC's where a plurality of regions of different through-plane thickness 78 may be accessed iteratively to provide optimum results.

The Programmable Analyzer 16 directs the rod 90 within the Reader Module 12 to actuate the valve 26 within the container 18 and thereby release the sample and colorant mixture into the chamber(s) 20. The analysis algorithm stored within the Programmable Analyzer 16 starts an internal timer when the sample is released into the chamber(s) 20, and the chemical analysis is performed at some time thereafter. Using the analysis algorithm for urinalysis, the Programmable Analyzer 16 positions the appropriate SE or LSE filters 58,66, if any, within the path of the light beam 54 within the field illuminator 40, and the light beam 54 selectively produced from the light source 44 and filtered within the field illuminator 40 is directed into a sample field quiescently residing within the chamber 20. The light emitted from the colorant within the sample passes back through the field illuminator 40 and into the image dissector 42 where it is converted into an electronic format in real time. The remaining analyses associated with a urinalysis may be performed in a second chamber or in a contiguous region of the same chamber 20. A more complete description of the performance of urine analysis using this apparatus 10 may be found in U.S. Pat. No. 6,004,821.

Although this invention has been shown and described with respect to the detailed embodiments thereof, it will be understood by those skilled in the art that various changes in form and detail thereof may be made without departing from the spirit and the scope of the invention. For example, the best mode of the apparatus 10 is described as being used with a particular sample container 18. Alternative containers may be used with the present invention apparatus. In addition, the field illuminator is described as having a light diverting prism 60 and a plurality of lens' 52, 56, and 67. Different filter positions, or no filters at all, may increase or eliminate the need for certain light diverting prisms and lens'.

What is claimed is:

1. An apparatus for testing a sample of biologic fluid quiescently residing within a chamber, said apparatus comprising:
    a field illuminator for selectively illuminating a field of the sample, said field having a known or ascertainable area;
    a positioner, which is operable to selectively change the position of one of the chamber or said field illuminator relative to the other of the chamber or said field illuminator, thereby permitting selective illumination of a plurality of said sample fields within the chamber;
    means for determining one of a through-plane thickness or a volume of each said sample field; and
    an image dissector, for converting an image of light passing through or emanating from each said field of the sample into an electronic data format useful for test purposes.

2. An apparatus according to claim 1, further comprising means for retrieving information concerning the chamber which information is used in the performance of one or more tests on the biologic fluid sample by said apparatus.

3. An apparatus according to claim 2, wherein said means for retrieving information includes a label reader for reading a label relating to the chamber.

4. An apparatus according to claim 3, wherein said label reader optically reads labels.

5. An apparatus according to claim 3, wherein said label reader magnetically reads labels.

6. An apparatus according to claim 3, further comprising:
    a programmable analyzer having a central processing unit;
    wherein said label reader transfers said information to said programmable analyzer, and said programmable analyzer interprets said information, identifying said one or more tests to be performed on the biologic fluid sample.

7. An apparatus according to claim 6, wherein said programmable analyzer contains a plurality of instructions for performing said one or more tests.

8. An apparatus according to claim 7, wherein said plurality of instructions are contained remote from said programmable analyzer and are accessed through said programmable analyzer.

9. An apparatus according to claim 7, wherein said plurality of instructions includes means for controlling said field illuminator and said positioner.

10. An apparatus according to claim 9, wherein said positioner includes means for spatially locating said chamber relative to said field illuminator;
    wherein said means for spatially locating said chamber relative to said field illuminator enables said field illuminator to be aligned with any particular spatial location within said chamber.

11. An apparatus according to claim 10, wherein a coordinate address is used to describe particular spatial locations within said chamber.

12. An apparatus according to claim 11, wherein said information retrieved by said label reader relates to features within the chamber.

13. An apparatus according to claim 1, wherein said field illuminator comprises;
    a light source which produces light within a wavelength range broad enough to be useful for a plurality of tests on the biologic fluid sample; and
    an assembly of objective optics, wherein said optics direct light emanating from said sample field or transmitted through said sample field into a known or ascertainable area image of light on said image dissector.

14. An apparatus according to claim 13, wherein said assembly of objective optics comprises:
    an objective lens;
    a focusing mechanism, said mechanism for selectively adjusting the position of said objective lens relative to the chamber; and
    a light filter for blocking or passing certain wavelengths of said light;
    wherein other wavelengths of said light emanating from said light source pass through said objective lens and said light filter and into said image dissector, or are blocked, respectively.

15. An apparatus according to claim 14, wherein said field illuminator directs light into said sample within the chamber and collects light fluorescing out of said sample.

16. An apparatus according to claim 15, wherein said light filter comprises:
a plurality of light source excitation filters;
a plurality of sample emission filters;
wherein said light source excitation filters block selected wavelengths of said light emanating from said light source and said sample emission filters block selected wavelengths of said light fluorescing out of said sample.

17. An apparatus according to claim 16, wherein said light source excitation filters are mounted on a first wheel and said sample emission filters are mounted on a second wheel and both said filters are rotatable into and out of a path of said light; and
wherein said field illuminator further comprises means for synchronizing said first wheel and said second wheel such that all desirable combinations of said light source excitation filters and said sample emission filters can be used during said tests.

18. An apparatus according to claim 16, wherein said field illuminator further comprises:
a light diverting prism; and
a reference detector having means for quantifying an energy level of said light emanating from said light source, wherein said quantified energy level is selectively used in evaluating said light fluorescing out of said sample.

19. An apparatus according to claim 14, wherein said field illuminator directs light into said chamber containing said sample and collects light produced by transmittance passing through said sample.

20. An apparatus according to claim 19, wherein said light filter comprises:
a plurality of light source excitation filters;
a plurality of sample emission filters;
wherein said light source excitation filters block wavelengths of said light emanating from said light source and said sample emission filters block wavelengths of said light emanating from said sample.

21. An apparatus according to claim 20, wherein said light source excitation filters are mounted on a first wheel and said sample emission filters are mounted on a second wheel and both said wheels permit rotation of said filters into and out of a path of said light; and wherein said field illuminator further comprises means for synchronizing said first wheel and said second wheel such that all desirable combinations of said light source excitation filters and said sample emission filters can be used during said tests.

22. An apparatus according to claim 21, wherein said field illuminator further comprises:
a light diverting prism; and
a reference detector having means for quantifying an energy level of said light emanating from said light source, wherein said quantified energy level is selectively used in evaluating said light emanating from said sample by fluorescence.

23. An apparatus according to claim 2, wherein said means for determining one of said through-plane thickness or said volume of said sample field includes said information retrieving means retrieving information from a label concerning the chamber which information includes one of said through-plane thickness of said sample field or said volume of said sample field.

24. An apparatus for testing a sample of biologic fluid, said apparatus comprising:
(a) a disposable container having a label and a chamber for quiescently holding the sample, said label containing information which is used in the performance of one or more tests on the biologic fluid sample quiescently residing within said chamber;
(b) a reader module which receives said disposable container, said reader module including:
a label reader for reading said attached label and thereby accessing said information;
a field illuminator for selectively illuminating a field of the sample, said sample field having a known or ascertainable area;
a positioner, which is operable to selectively change the position of one of said chamber or said field illuminator relative to the other of said chamber or said field illuminator, thereby permitting selective illuminating of a plurality of said sample fields within said chamber; and
means for spatially locating said chamber relative to said field illuminator;
wherein said means for spatially locating said chamber relative to said field illuminator enables said field illuminator to be aligned with a particular spatial location within said chamber;
an image dissector, for converting an image of light passing through or emanating from each said sample field into an electronic data format useful for test purposes; and
means for determining one of a through-plane thickness or a volume of said sample field.

25. An apparatus for testing a sample of biologic fluid, said apparatus comprising:
(a) a disposable container having a label and a chamber for quiescently holding the sample, said label containing information which is used in the performance of one or more tests on the biologic fluid sample quiescently residing within said chamber;
(b) a reader module which receives said disposable container, said reader module including:
a label reader for reading said attached label, and thereby accessing said information;
a field illuminator for selectively illuminating a field of the said sample,
said sample field having a known or ascertainable area;
a positioner, which is operable to selectively change the position of one of said chamber or said field illuminator relative to the other of said chamber or said field illuminator, thereby permitting selective illumination of a plurality of said sample fields within said chamber; and
means for spatially locating said chamber relative to said field illuminator;
wherein said means for spatially locating said chamber relative to said field illuminator enables said field illuminator to be aligned with a particular spatial location within said chamber; and
means for determining one of a through-plane thickness or a volume of said sample field.

* * * * *

UNITED STATES PATENT AND TRADEMARK OFFICE
CERTIFICATE OF CORRECTION

PATENT NO. : 6,866,823 B2
DATED : March 15, 2005
INVENTOR(S) : Wardlaw

It is certified that error appears in the above-identified patent and that said Letters Patent is hereby corrected as shown below:

Column 16,
Line 44, please delete ";" and insert -- : --.

Column 18,
Lines 19-20, please delete "illuminating" and insert -- illumination --.

Signed and Sealed this

Seventeenth Day of May, 2005

JON W. DUDAS
*Director of the United States Patent and Trademark Office*